United States Patent [19]

Laruelle et al.

[11] Patent Number: 4,518,587
[45] Date of Patent: May 21, 1985

[54] DIPEPTIDES OF L-5-HYDROXYTRYPTOPHAN, PROCESSES FOR THEIR PREPARATION AND DRUGS IN WHICH THEY ARE PRESENT

[75] Inventors: Claude Laruelle, Villeneuve Loubet; Marcel Lepant, Vence; Bernard Raynier, Cagnes, all of France

[73] Assignee: S.A. Panmedica, Carros, France

[21] Appl. No.: 611,987

[22] Filed: May 18, 1984

[30] Foreign Application Priority Data

May 24, 1983 [FR] France .................. 83 08493

[51] Int. Cl.³ .................. A61K 37/00; C07C 103/52
[52] U.S. Cl. .................. 514/19; 260/112.5 R
[58] Field of Search .................. 260/112.5 R; 424/274, 424/177

[56] References Cited

U.S. PATENT DOCUMENTS 4,187,295  2/1980  Pless et al. .................. 260/112.5 R
4,456,611  6/1984  Laruelle et al. .................. 424/274

OTHER PUBLICATIONS

J. Chem. Soc., (c), (1968), 910–915.
Chem. & Pharm. Bull., vol. 30, (1982), 4435–4443.
Chem. Abstr., vol. 68, (1968), 105514.
Chem. Abstr., vol. 91, (1979), 134784.

*Primary Examiner*—Delbert R. Phillips
*Attorney, Agent, or Firm*—Oblon, Fisher Spivak, McClelland and Maier

[57] ABSTRACT

The present invention relates to new dipeptides of L-5-hydroxytryptophan.

They correspond to the general formula below:

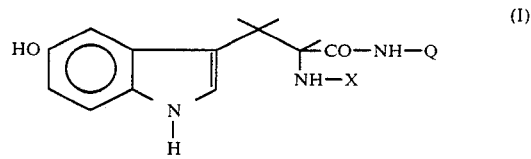

in which:

X represents hydrogen or a lower acyl radical and
Q represents a free or esterified aminoacid radical.

Application: drugs for combating disorder of the serotoninergic system.

6 Claims, No Drawings

DIPEPTIDES OF L-5-HYDROXYTRYPTOPHAN, PROCESSES FOR THEIR PREPARATION AND DRUGS IN WHICH THEY ARE PRESENT

FIELD OF THE INVENTION

The present invention relates to new dipeptides of L-5-hydroxytryptophan, the processes for their preparation and drugs in which the said derivatives are present.

PRIOR ART

The particularly important function of serotonin as a neuromediator is known and its influence in the mechanism of sleep and in certain types of nervous depression has been widely studied. The Applicant Company, which has great experience in the field of serotonin derivatives (cf. especially French Pat. No. 2,499,076) has contributed towards demonstrating important interactions between the serotoninergic system and the other cholinergic or dopaminergic systems. Any disorder of the serotoninergic system thus has direct consequences, such as depression, or indirect consequences by repercussion on the synaptic levels of the other endogenic amines, the serotonin appearing to be involved in certain syndromes of parkinsonism or in Alzheimer's disease. This disorder can be corrected by the administration of L-5-hydroxytryptophan (L-5-HTP), which is a direct precursor of serotonin (5-HT). It is known, however, that the oral administration of L-5-HTP only permits a small increase in its level in the brain (cf. French Pat. No. 2,499,076 already cited). A rather mediocre passage through the blood-brain barrier and a substantial peripheral decarboxylation therefore make it necessary to administer large quantities of L-5-HTP.

SUMMARY OF THE INVENTION

The object of the present invention was to provide a new family of L-5-HTP derivatives making it possible to correct the brain levels of 5-HTP and 5-HT at relatively low doses permitted by an excellent passage through the digestive and blood-brain barriers and also by a low level of peripheral decarboxylation. As their toxicities are moreover lower than that of L-5-HTP, the therapeutic index from the point of view of the serotoninergic activity is considerably increased.

The present invention relates to dipeptides of L-5-hydroxytryptophan of the general formula I below:

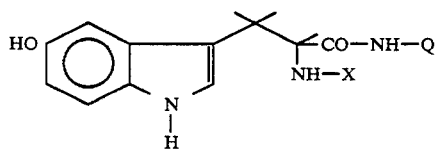

(I)

in which:
X represents hydrogen or a lower acyl radical and
Q represents hydrogen or an aminoacid radical in which the reactive group or groups may or may not be substituted, and to their pharmaceutically compatible addition salts with acids or bases.

The present invention also relates to a process for the preparation of the dipeptides according to the present invention, which comprises:
(a) preparing a derivative blocked on the nitrogen in the α-position of the L-5-hydroxytryptophan,
(b) preparing a blocked derivative of an aminoacid leaving only the —NH₂ group as the reactive group,
(c) condensing the two blocked products in the presence of a condensation agent, in a suitable solvent, at a temperature of between 0° and 30° C., and
(d) if appropriate, unblocking the protected groups.

In an advantageous embodiment of the process forming the subject of the present invention, the blocking groups on the nitrogen in the α-position of the L-5-hydroxytryptophan (5-HTP) are chosen from carbobenzyloxycarbonyl, paramethoxybenzyloxycarbonyl and tert.-butoxycarbonyl radicals and DANE salts (E. DANE, Angew. Chem. Int. Ed. 1962, 1, 658) with acetylacetone or ethyl acetoacetate.

In another advantageous embodiment of the process forming the subject of the present invention, the blocking of the acid group or both the acid groups of the aminoacid is effected with the aid of compounds chosen from the group comprising esters of primary, secondary or tertiary alcohols and benzyl esters.

In a particularly advantageous embodiment of the process forming the subject of the present invention, the L-5-hydroxytryptophan blocked on the nitrogen in the α-position is used in the form of a reactive ester, the said ester being chosen from cyanomethyl, 4-nitrophenyl and pentachlorophenyl esters.

According to the invention, the condensation of the blocked products is effected in the presence of dicyclohexylcarbodiimide in a solvent taken from the group comprising dimethylformamide, dimethyl sulfoxide, pyridine, chloroform, methylene chloride, tetrahydrofuran and acetone.

Also according to the invention, the unblocking of the protected groups is effected by catalytic hydrogenation or controlled hydrolysis.

In addition to the above provisions, the invention also comprises further provisions, which will become apparent from the description which now follows.

The present invention will be understood more clearly with the aid of the remainder of the description which now follows, which includes practical examples of the process for the preparation of the new derivatives according to the invention, together with a review of pharmacological experiments.

It must be clearly understood, however, that these examples and this review are given solely by way of illustration and in no way imply a limitation.

It should be noted that all the products were subjected to analysis by thin layer chromatography and show only a single spot.

The thin layer chromatography (TLC) was carried out on Kieselgel (silica gel) F 254 plates, which were developed in the following systems:
A—butanol 8/acetic acid 1/water 1
B—acetonitrile 85/water 10/acetic acid 5 and disclosed under ultraviolet light at 254 nm.

The results of the elemental analyses carried out on all the products are consistent with the theoretical formulae.

PREPARATION EXAMPLES
EXAMPLE 1— DIETHYL 5-HYDROXY-L-TRYPTOPHYL-L-ASPARTATE (a) Diethyl N-benzyloxycarbonyl-5-benzyloxycarbonyloxy-L-tryptophyl-L-aspartate In a suitably equipped 2 liter apparatus, 34.16 g (70 mmol) of L-N,O-bisbenzyloxycarbonyl-5-hydroxytryptophan, prepared according to French Pat. No. 2,499,076, are added, under nitrogen, to 500 ml of pure dry chloroform free of ethanol. Diethyl aspartate, obtained by mixing 15.80 g (70 mmol) of diethyl L-aspartate hydrochloride with 7.44 g (73.5 mmol) of triethylamine in 200 ml of pure chloroform, is added rapidly. The resulting solution is cooled to about $+5°$ C. and a solution of 15.90 g (77 mmol) of dicyclohexylcarbodiimide in 100 ml of pure chloroform is added slowly over a period of 45 minutes. The mixture is then stirred at ambient temperature. The reaction, which can be followed by TLC, is complete in 48 hours. After the solvent has been evaporated off, the product is taken up with acetone, enabling the dicyclohexylurea to be separated off. The solvent is again evaporated off, the residue is taken up with chloroform and the mixture is washed with water, then with a dilute solution of sodium bicarbonate, then with a dilute solution of hydrochloric acid and finally with water. After drying over anhydrous sodium sulfate, the chloroform layer is diluted with ethyl ether.

After a few days at $+5°$, the solution yields crystals of diethyl N,O-bisbenzyloxycarbonyl-5-hydroxytryptophylaspartate (24.30 g) (yield: 52.7%). The product shows a single spot of Rf=0.9 in TLC on a silica plate in the system chloroform 1:acetone 1.

(b) Diethyl 5-hydroxy-L-tryptophyl-L-aspartate

A solution of 24 g (36 mmol) of the product obtained above in 100 cc of acetic acid and 300 cc of ethanol is hydrogenated under atmospheric pressure, at 40°–50° C., in the presence of 2 g of 5% palladium-on-charcoal. After the catalyst has been filtered off, the solvent is evaporated off and the residue is taken up with ethyl ether, yielding 9.8 g (25 mmol) of crystals. Recrystallization can be carried out from 50 volumes of cyclohexane to give a pure product having the following analytical characteristics:

TLC on a Kieselgel plate in system A (butanol 8/acetic acid 1/water 1): a single spot of Rf 0.65.

NMR spectrum in solution in $CD_3CN$, relative to TMS: to 8 ppm (m) broad $NH_2$; 7.2 to 6.5 ppm (m) 4H (arom); 4.7 ppm (m) (1H)—($NH_2$)—CH—CONH; 4.3 to 3.8 ppm 2 (q) $4H2OCH_2CH_3$; $\overline{3.6}$ ppm (m) 1H, CON$\underline{H}$CHCOO; 3 ppm (m) (2H) $CH_2CH(NH_2)$—CO; 2.7 ppm (m) (2H) $CH_2COO$; 1.15 (t) (6H) 2—OCH$_2$CH$_3$.

Infra-red spectrum (KBr): 3300 cm$^{-1}$ $NH_2$; 1740 cm$^{-1}$ (vs) ester; 1650 cm$^{31\ 1}$ (vs) amide; 1550 cm$^{-1}$ (s) amide; 1200/1250 cm$^{-1}$ ester.

(c) Diethyl L-5-hydroxytryptophyl-L-aspartate hydrochloride 3.70 g (9.5 mmol) of the product obtained above according to (b) are dispersed in water, 9.5 ml of normal hydrochloric acid are added and the solution is treated with active charcoal and then lyophilized. This gives an amorphous solid which has an unsharp m.p. of between 90° and 100° and whose NMR spectrum recorded in $D_2O$ has the same characteristic signals as the base obtained according to (b).

EXAMPLE 2—5-HYDROXY-L-TRYPTOPHYL-L-ASPARTIC ACID (a) Dibenzyl N-benzyloxycarbonyl-5-hydroxy-L-tryptophanylaspartate 58.2 g (0.12 mmol) of dibenzyl L-aspartate paratoluenesulfonate, prepared according to A. K. BOSE and R. E. STRUBE [J. of Pharm. Sc. 9, 847 (1963)], are added to 300 ml of rigorously pure chloroform, the temperature of the medium is lowered to about $+8°$ C. and 17 ml of triethylamine are added. After about 30 minutes, 43.5 g (0.12 mol) of L-N-benzyloxycarbonyl-5-hydroxytryptophan (prepared, for example, according to French Pat. No. 2,499,076), dissolved in 800 ml of chloroform, are added. A solution of 24.8 g (0.12 mol) of dicyclohexylcarbodiimide in 100 ml of chloroform is then added. After stirring for 48 hours at ordinary temperature, the insoluble material is filtered off, the filtrate is evaporated and the residue is then taken up twice in succession with acetone in order to separate off the traces of dicyclohexylurea. After taking up with ether, a pure product of m.p.=177° C. and $[\alpha]_D = -22.3°$ (C=1, acetone) is obtained. TLC on Kieselgel in the system toluene 10/ethyl formate 10/formic acid 1 gives a single spot of Rf=0.70.

(b) 5-Hydroxy-L-tryptophyl-L-aspartic acid trihydrate 32 g (0.05 mol) of the derivative obtained above according to (a) are dissolved in 600 ml of acetic acid and 600 ml of ethanol and the solution is hydrogenated at atmospheric pressure in the presence of 3 g of 5% palladium-on-charcoal. When the absorption of hydrogen has ended, the mixture is filtered, the filtrate is evaporated, the residue is made into a paste again with ether and the product is recrystallized from water. This gaves 86% of the trihydrate of the title derivative of m.p. 190° C. and $[\alpha]_D = +12.40°$ (C=1, 0.1N $NH_4OH$). TLC of the product on a Kieselgel plate in the system isopropanol 2/ethyl acetate 2/water 1/acetic acid 0.1 gives a single spot of Rf=0.65.

EXAMPLE 3—DIETHYL 5-HYDROXY-L-TRYPTOPHYL-L-GLUTAMATE HYDROCHLORIDE (a) Diethyl N-benzyloxycarbonyl-5-hydroxy-L-tryptophyl-L-glutamate 33.5 g (0.14 mol) of diethyl glutamate hydrochloride, prepared according to Brenner (Helv. 36, 1109 (1053)), are added, at 0° C., to 300 ml of pure chloroform, and 19.5 cc of triethylamine are introduced dropwise. 50 g (0.14 mol) of L-N-benzyloxycarbonyl-5-hydroxytryptophan (prepared according to French Pat. No. 2,499,076) are then added and a solution of 29 g of dicyclohexylcarbodiimide in 100 ml of chloroform is added slowly. The mixture is stirred for 24 hours at ordinary temperature, the urea is then filtered off and the filtrate is evaporated to dryness. The residue is taken up a further twice with 200 ml of acetone in order to remove by filtration the dicyclohexylurea which is still present. The filtrate is evaporated, the residue is washed with water by making a paste and the crude product is then recrystallized from ethyl acetate; this gives pure diethyl L-N-benzyloxycarbonyl-5-hydroxytryptophyl-L-glutamate of m.p.=154/5° C. with a yield of 69%. The product gives a single spot in TLC on Kieselgel in system A (butanol 8/acetic acid 1/water 1) of Rf=0.95. $[\alpha]_D = -28°$ (C=1, acetone).

(b) Diethyl 5-hydroxy-L-tryptophyl-L-glutamate hydrochloride 50 g (93 mmol) of the above product are hydrogenated in 250 ml of acetic acid in the presence of 3 g of 5% palladium-on-charcoal. After the solvent has been evaporated off, the residue is taken up with water and the mixture is neutralized to pH 7.0 with dilute aqueous ammonia and extracted with ethyl acetate. After the solvent has been evaporated off, the residue is taken up with 170 ml of ethanol, and 21 ml of a 4M solution of hydrochloric acid in ethanol are added. The mixture is then evaporated at low temperature and the residue is solidified with ether. The product shows a single spot in TLC on Kieselgel in system A (butanol 8/acetic acid 1/water 1) of Rf=0.60. $[\alpha]_D = +2.9°$ (C=1, water). The NMR spectrum in solution in $D_2O$ has the following characteristics: 7.5 to 6.7 ppm (m) (arom) (4H); 4.1 (ppm) 2 (q) (4H) $OCH_2CH_3$; 3.2 ppm (d) (2H) $CH_2CH(NH_3)^{(+)}$; 2.0 ppm (m) (4H) $CH_2$—CHHD 2; 1.10 ppm 2 (t) (6H) 2—$OCH_2CH_3$. IR spectrometry in KBr shows the following absorptions: 3500 to 2500 $cm^{-1}$—broad unresolved signals COOH and $NH_3^+$; 1730 $cm^{-1}$ ester (vs); 1670 $cm^{-1}$ amide (s); 1200 $cm^{-1}$ (ester).

EXAMPLE 4—5-HYDROXY-L-TRYPTOPHYL-L-GLUTAMIC ACID (a) Dibenzyl L-benzyloxycarbonyl-5-hydroxytryptophyl-L-glutamate 32.5 g (65 mmol) of L-dibenzyl glutamate paratoluenesulfonate, prepared according to A. K. BOSE and R. E. STRUBE (J. of Pharm. Sc. 9, 847 (1963)), are suspended in 300 ml of pure chloroform, 65 mmol of triethylamine are added, the mixture is stirred for 30 minutes and 23 g (65 mmol) of L-N-benzyloxycarbonyl-5-hydroxytryptophan, prepared according to French Pat. No. 2,499,076, dissolved in 50 ml of pure chloroform and 50 ml of pure acetone, are then added. Finally, a solution of 13.4 g (65 mmol) of dicyclohexylcarbodiimide in 50 ml of chloroform is introduced slowly. After a few hours, the reaction is complete and the mixture is diluted copiously with acetone in order to precipitate the dicyclohexylurea completely. The solution is evaporated, the residue is taken up with ethyl acetate and the mixture is washed with slightly acidic water, with dilute sodium hydroxide solution and then finally with water. After drying over dry sodium sulfate, the mixture is evaporated and the residue is recrystallized from isopropanol to give 80% of pure dibenzyl L-N-benzyloxycarbonyl-5-hydroxytryptophyl-L-glutamate of m.p.=150° C. and of $[\alpha]_D = -25.5°$ (C=1, acetone), which, in TLC on Kieselgel in the system toluene 10/ethyl formate 10/formic acid 1, shows a single spot of Rf=0.50.

The product also has the following spectral characteristics:

NMR in solution in $CDCl_3$, relative to TMS: 8.0 ppm (s) (1H) OH phenol; 7.90 ppm (s) (5H) (ar) benzyl; 7.2 to 6.5 ppm (m) (4H) arom; 5.7 and 5.5 ppm 2 (m) (2H) N—H; 5.0 ppm 2 (s) (6H) $CH_2$—Ar; 4.6 ppm (m) (2H) $CH(NH)CO$; 3.2 ppm (m) 2H Ar—$CH_2$—CH—CO; 2.1 ppm (m) (4H)—$CH_2$—$CH_2$. IR in KBr: 3450 and 3300 $cm^{-1}$ (s) —NH; 1735 $cm^{-1}$ (vs) ester; 1690 $cm^{-1}$ (s); 1655 $cm^{-1}$ and 1530 $cm^{-1}$ (vs) amide; 1215 $cm^{-1}$ ester.

(b) 5-Hydroxy-L-tryptophyl-L-glutamic acid 25 g (38 mmol) of the above product are hydrogenated in 200 ml of acetic acid in the presence of 2.5 g of 5% palladium-on-charcoal. The mixture is evaporated to dryness and the residue is first taken up with ethyl acetate and then recrystallized from 20 volumes of water; this gives 62% of L-5-hydroxytryptophyl-L-glutamic acid of m.p. 230/2° C., purity 99.7% and $[\alpha]_D = +17.6°$ (C=1, N/10 aqueous ammonia), which, in NMR spectrometry in trifluoroacetic acid, has the following characteristics: 7.5 to 6.5 ppm (m) (5H) arom; 4.5 ppm (m) (2H) $CH(NH)CO$; 3.25 ppm (m) (2H) Ar$CH_2$CHCO 2.3 to 2.0 ppm (m) (4H) $CH_2$—$CH_2$.

EXAMPLE 5—METHYL ESTER OF 5-HYDROXY-L-TRYPTOPHYL-L-TYROSINE HYDROCHLORIDE (a) Pentachlorophenyl ester of N-benzyloxycarbonyl-5-hydroxy-L-tryptophan 115 g of L-N-benzyloxycarbonyl-5-hydroxytryptophan, prepared according to French Pat. No. 2,499,076, and 86 g (0.325 mol) of pentachlorophenol are added to 1.2 liters of tetrahydrofuran, and a solution of 67 g (0.325 mol) of dicyclohexylcarbodiimide in 200 ml of tetrahydrofuran is then added.

After stirring for 20 hours at ordinary temperature, the dicyclohexylurea is filtered off, the filtrate is evaporated, the residue is taken up with ethyl acetate and the mixture is washed successively with 1N hydrochloric acid, 0.1N sodium hydroxide solution and water; after drying over sodium sulfate, the mixture is evaporated to dryness under reduced pressure. The residue is taken up with petroleum ether to give the title derivative in the form of crystals of m.p. 135/140° C. with a yield of 80%.

(b) Methyl ester of N-benzyloxycarbonyl-5-hydroxy-L-tryptophyl-L-tyrosine 9.3 g (0.04 mol) of the methyl ester of L-tyrosine hydrochloride are added to 50 ml of dimethylformamide, and a solution of 0.04 mol of triethylamine and 24 g (0.04 mol) of N-benzyloxycarbonyl-5-hydroxytryptophan (PCP ester) according to (a) in 50 ml of dimethylformamide is then added at 0° C. The mixture is left to return to ambient temperature and stirred for 20 hours. It is then introduced into excess cold water. The precipitate is taken up with ethyl acetate and the mixture is washed with normal hydrochloric acid, with decinormal sodium hydroxide solution and then with water. After drying over sodium sulfate, the solution is evaporated to dryness and the product is chromatographed on a silica column in the system chloroform 3/acetone 1. This gives 42% of a product of m.p. 130/3° C. and $[\alpha]_D = -18.5°$ (C=1, acetone), which has the following spectral characteristics in NMR (DMSO-$d_6$): 10 ppm (s) (1H)OH phenol; 9 ppm (s) (1H) OH phenol; 8 ppm (m) (2H)—NH—; 7.2 ppm (s) (5H) phenyl; 7.0 to 6.7 ppm (m) (9H) arom; 4.8 ppm (s) (2H) $CH_2$—benzyl—; 4.3 ppm (m) (2H) —$CH(NH)$—CO; 3.5 ppm (s) (3H)$OCH_3$; 2.8 ppm (m) (4H)—$CH_2$—; and in infra-red (KBr): 3400-3300 $cm^{-1}$ OH and NH; 1730 $cm^{-1}$ ester; 1680 cm$^{-1}$ NH CO—OCH$_2$; 1650 and 1550 cm$^{-1}$ CONH; 1220 cm$^{-1}$ ester.

(c) Methyl ester of 5-hydroxy-L-tryptophyl-L-tyrosine hydrochloride

The product obtained above is hydrogenated in 300 ml of ethanol and 1 ml of acetic acid in the presence of 1 g of 5% palladium-on-charcoal. After filtration, the filtrate is evaporated under reduced pressure and the residue is then taken up with water to which hydrochloric acid has been added. The mixture is treated with active charcoal and lyophilized. This gives 90% of beige crystals of purity 97% in anhydrous titrimetry and of $[\alpha]_D = -11.6°$ (C=1, water).

EXAMPLE 6—METHYL ESTER OF N-ACETYL-5-HYDROXY-L-TRYPTOPHYL-L-TYROSINE (a) N-Acetyl-5-hydroxy-L-tryptophan A suspension of 88 g (0.4 mol) of L-5-HTP in 400 ml of water is cooled to about +5° C. and 61 ml of acetic anhydride and a dilute solution of sodium hydroxide are introduced simultaneously in order to keep the pH between 7 and 7.5. The reaction is complete after two hours and the mixture is cooled to 0° C. and acidified slowly with dilute HCl. The precipitated L-N-acetyl-5-acetyloxytryptophan derivative is filtered off and dried. M.p. 167/169° C. It is added at a rate of about 15% to a saturated ethanolic solution of ammonia. After stirring overnight at ordinary temperature, a white precipitate appears, which is filtered off and washed. This precipitate is dissolved in water and, after acidification, the aqueous solution yields crystals of L-N-acetyl-5-hydroxytryptophan, which can be recrystallized from 5 volumes of water: m.p.=209° C. $[\alpha]_D = +13.4°$ (C=1, 0.1N aqueous ammonia); $-13.1°$ (C=1, ethanol).

The acidimetric titer is 99%. The spectral characteristics are as follows: in NMR (in D$_2$O): 7.2 ppm (d) (1H) J=8 Hz 1H; 7.10 ppm (s) (1H); 7.0 ppm (1H) (d) J'=2 Hz; 6.70 ppm dd (1H); 4.5 ppm (m) (1H) CH (NH)CO; 3.1 ppm (m) (2H) —CH$_2$—; 1.8 ppm (s) (3H) CH$_3$CO; in infra-red (in KBr): 3440, 3400, 3320 cm$^{-1}$ NH,OH; 2500 to 1800 cm$^{-1}$ unresolved signals COOH; 1690 cm$^{-1}$ COOH-1630 and 1550 cm$^{-1}$ —CONHR.

(b) Methyl ester of N-acetyl-5-hydroxy-L-tryptophyl-L-tyrosine 14 g (60 mmol) of the methyl ester of L-tyrosine hydrochloride are dissolved in 30 ml of water, the base is freed by the addition of NaHCO$_3$ and the tyrosine ester base is extracted with ethyl acetate; it crystallizes in the cold.

After filtration and drying, 46 mmol of the tyrosine ester base are mixed with 46 mmol of L-N-acetyl-5-hydroxytryptophan, obtained according to (a), in 100 ml of tetrahydrofuran and 100 ml of acetone. 46 mmol of dicyclohexylcarbodiimide are added and the mixture is stirred for 24 hours. The precipitated urea is filtered off, the solvent is evaporated off, the residue is taken up with ethyl acetate and the mixture is washed with dilute hydrochloric acid, with decinormal sodium hydroxide solution and finally with water. After the solvent has been evaporated off, the residue is recrystallized from an ethanol/ether mixture. This gives the title derivative in the form of beige crystals of m.p. 176° C. and $[\alpha]_D = -15.40°$ (C=1, acetone) and $[\alpha]_D = -9.2°$ (C=1, ethanol), the physico-chemical characteristics of which are listed below: NMR spectrometry (acetone-d$_6$): 9.5 ppm (m) (1H) OH phenol; 8.3 (s) (1H) OH phenol; 7.8 to 6.7 ppm (m) (11H) arom and —NH—; 4.7 (t) (2H) CH(NH)CO; 3.6 ppm (s) (3H)—OCH$_3$; 3 ppm (m) (4H) —CH$_2$—; 1.85 ppm (s) (3H) CH$_3$CO; infra-red spectrometry (KBr): 3400-3300 cm$^{-1}$ (vs) OH, NH; 1735 cm$^{-1}$ (s) ester; 1650-1630 and 1560-1530 cm$^{-1}$ CONH (s).

EXAMPLE 7—METHYL ESTER OF N-ACETYL-5-HYDROXY-L-TRYPTOPHYL-5-HYDROXY-L-TRYPTOPHAN 22 g (94 mmol) of the methyl ester of L-5-hydroxy-tryptophan, obtained according to H. TAMIR (J. of Neurochem. 32, 593-8 (1979)), and 24 g of L-N-acetyl-5-hydroxy-L-tryptophan, obtained according to Example 6—a), are dissolved in 500 ml of tetrahydrofuran and 50 ml of DMF, and a solution of 21 g of dicyclohexylcarbodiimide in 100 ml of THF is then added at ordinary temperature. After stirring for 20 hours at ordinary temperature, the precipitated urea is filtered off, the solvent is evaporated off under reduced pressure and the residue is taken up in ethanol, from which the product is precipitated by the addition of petroleum ether. The crude product is chromatographed on silica in acetone. This gives 60% of an amorphous product showing a single spot of Rf 0.25 in TLC on Kieselgel in the system toluene 10/ethyl formate 10/formic acid 1/ethanol 0.5. $[\alpha]_D = +10.1°$ (C=1, acetone). The mass spectrum and elemental analysis confirm the structure of the product, which also has the following characteristics:

In NMR (DMSO-d$_6$): 10 ppm (m) (2H) OH phenol; 9/8.5 ppm (m) (2H) NH; 7.2 to 6.5 ppm (m) (8H) arom; 4.5 ppm (m) (2H) CH (NH) CO; 3.5 ppm (s) (3H) COOCH$_3$; 3.0 ppm (m) (4) —CH$_2$—; 1.7 ppm (s) (3H) CH$_3$CO.

EXAMPLE 8—5-HYDROXY-L-TRYPTOPHYL-L-ALANINE HYDRATE 0.1 mol of the benzyl ester of L-alanine paratoluenesulfonate, prepared according to GIBIAN (Ann. 642, 145 (1961)), is added to 500 ml of pure chloroform containing 0.1 mol of TEA.

After 30 minutes, a solution of 0.1 mol of L-N-benzyloxycarbonyl-5-hydroxytryptophan in 200 ml of acetone is then added, followed by 0.1 mol of dicyclohexylcarbodiimide, and the mixture is stirred at ordinary temperature until the reaction has ended. The mixture is filtered, the material on the filter is washed copiously with acetone and the organic solution is evaporated. The product, solidified in ether, is in the form of attractive white crystals of m.p.=183° C. and $[\alpha]_D^{30} = -22.3°$ (C=1, acetone).

This product is hydrogenated in 10% solution in acetic acid in the presence of palladium. After the solvent has been evaporated off, the residue is recrystallized from water. This gives the title derivative with a yield of 64%. The m.p. is 260/300° C. (dec); $[\alpha]_D^{30} = +11.3°$ (C=1, N HCl); TLC in system B shows a single spot of Rf=0.45. Analysis of the water according to K. FISHER indicates a content of 5.6%, confirming the existence of the monohydrate.

EXAMPLE 9—5-HYDROXY-L-TRYPTOPHAN-L-VALINE 0.1 mol of triethylamine is added, at +5° C., to 0.1 mol of the benzyl ester of L-valine paratoluenesulfonate, prepared according to ZERVAS (J.O.C. 22, 1520 (1957)), suspended in 500 ml of pure chloroform, and a solution of 0.1 mol of L-N-benzyloxycarbonyl-5-hydroxytryptophan in 200 ml of acetone is then added. A solution of 0.1 mol of dicyclohexylcarbodiimide in 50 ml of chloroform is then introduced slowly and the mixture is stirred at ordinary temperature until the condensation has ended. After filtration, the organic solution is evaporated, the residue is then taken up with ethyl acetate and the mixture is washed carefully with acidified water, with dilute sodium hydroxide solution and then with water. After drying and evaporation of the solvent, the residue is taken up several times and finally recrystallized from a benzene/acetone mixture.

This gives the benzyl ester of L-N-benzyloxycarbonyl-5-hydroxytryptophyl-L-valine in the form of white crystals of m.p. 174° C. and $[\alpha]_D^{25} = -23.3°$ (C=1, acetone).

This product is subjected to catalytic hydrogenation in acetic acid solution in the presence of palladium-on-charcoal. After filtration and evaporation, the residue, taken up with toluene and then with chloroform, is recrystallized from an isopropanol/acetone mixture. The title derivative is obtained in the form of crystals of m.p. 208° C., which show a single spot of Rf=0.50 in TLC in system B. The product crystallizes in the form of a solvate with isopropanol, as shown by elemental analysis and the NMR spectrum (DMSO), the latter having the following characteristic signals: 10.1 ppm (s) (1H), phenol; 8.0 ppm (m, broad) (1H), —NH—; 7.2 to 6.7 ppm (m) (4H) arom; 5.2 ppm broad OH band masking $\underline{CH}(NH_2)$—CO; 1.4 ppm (d) (6H) $(CH_3)_2CHOH$; 0.9 ppm (d) (6H) $(CH_3)_2$—CH—.

EXAMPLE 10—5-HYDROXY-L-TRYPTOPHYL-L-LEUCINE 0.1 mol (39.4 g) of the benzyl ester of L-leucine paratoluenesulfonate, prepared according to ZERVAS (J.O.C. 22, 1520 (1957)), and 0.1 mol of triethylamine are added to 500 ml of chloroform. After stirring for one hour, a solution of 0.1 mol (35.4 g) of N-benzyloxycarbonyl-L-5-hydroxytryptophan in 200 ml of acetone and a solution of 0.1 mol of dicyclohexylcarbodiimide in 50 ml of chloroform are introduced and ordinary temperature is maintained until the reaction has ended. After the mixture has been filtered, the filtrate evaporated, the residue taken up with ethyl acetate and this organic solution washed in the usual way, the latter is evaporated to dryness. The amorphous residue is first taken up with ether and then recrystallized from isopropanol.

This gives the benzyl ester of L-N-benzyloxycarbonyl-5-hydroxytryptophyl-L-valine in the form of crystals of m.p.=159° C. and of $[\alpha]_D^{25} = -15.2°$ (C=1, acetone), which is subjected to catalytic hydrogenolysis in acetic acid solution in the presence of palladium. The evaporation residue is finally recrystallized from ethanol. This gives the title derivative in the form of a solvate containing one molecule of ethanol, of m.p.=164° C., which, in TLC, gives a spot of Rf=0.45 in system B.

The NMR spectrum (D$_2$O) has the following characteristic signals: 7.4 ppm (d) (1H) (J=9 Hz); 7.3 ppm (s) (1H); 7.15 ppm (d) (1H) J'=2 Hz; 6.85 ppm (dd) (1H), J'=2 Hz J=9 Hz, (arom); 4.3 ppm (m) (2H) —$\underline{CH}$(NH)—CO; 3.7 ppm (q) (2H) $CH_3\underline{CH_2}OH$; 3.2 ppm (m) (2H)—$CH_2$—CO; 1.5 ppm (m) (2H)—$CH_2$—; 1.15 ppm (t) (3H) $\underline{CH_3}CH_2OH$; 0.7 ppm (m) (7H)—$CH(CH_3)_2$—.

EXAMPLE 11—5-HYDROXY-L-TRYPTOPHYL-L-PROLINE 0.1 mol of the benzyl ester of L-proline hydrochloride, obtained according to RAMACHANDRAN (Journal of Organic Chemistry 28, 173/177 (1963)), is dissolved in 500 ml of pure chloroform, and 0.1 mol of triethylamine is added in the cold. After a few minutes, the reaction medium is treated with a solution of 0.1 mol of L-N-benzyloxycarbonyl-5-hydroxy-tryptophan in 200 ml of acetone and then with a solution of 0.1 mol of dicyclohexylcarbodiimide in 50 ml of chloroform. The mixture is left to return to ambient temperature and stirred until the reaction has ended. It is filtered, the filtrate is evaporated to dryness, the residue is taken up with ethyl acetate and the mixture is washed in the usual way, dried and then evaporated. The product is then chromatographed on a silica column in a chloroform/acetone mixture to give 40% of the benzyl ester of L-N-benzyloxycarbonyl-5-hydroxytryptophyl-L-proline of $[\alpha]_D = -33.9°$ (C=1, acetone), which is subjected to hydrogenolysis in acetic acid in the presence of palladium.

The final product is recrystallized from an acetone/ethanol mixture. This gives L-5-hydroxytryptophyl-L-proline of m.p. 162/3°, which, in TLC in system B, shows a single spot of Rf=0.7. $[\alpha]_D = -8.4°$ (C=1, N HCl).

EXAMPLE 12—5-HYDROXY-L-TRYPTOPHYL-L-PHENYLALANINE 86 mmol (36.75 g) of the benzyl ester of L-phenylalanine paratoluenesulfonate, prepared according to ZERVAS (J.O.C. 22, 1520 (1957)), are added to 500 ml of chloroform, and 86 mmol of triethylamine are then added at 0/+5° C. After a few minutes, a solution of 86 mmol of L-N-benzyloxycarbonyl-5-hydroxytryptophan in 500 ml of acetone and a solution of 90 mmol of dicyclohexylcarbodiimide in 50 ml of chloroform are added, still in the cold. After one night at ambient temperature, the mixture is evaporated, the residue is taken up with ethyl acetate, the urea formed is filtered off and the organic solution is washed in the usual way. After drying and evaporation, the residue is solidified in ether and then recrystallized from ethanol. This gives 55% of the benzyl ester of L-N-benzyloxycarbonyl-5-hydroxytryptophyl-L-phenylalanine in the form of crystals of m.p.=202°. This derivative is hydrogenated in 10% solution in acetic acid in the presence of palladium, and then recrystallized from ethanol. This gives 80% of L-5-hydroxytryptophyl-L-phenylalanine of m.p.=260° C. (dec), which, in TLC in system B, shows a single spot of Rf=0.4 and $[\alpha]_D^{25} = -31°$ (C=1, DMF). Elemental analysis, confirmed by NMR, shows the existence of a solvate containing one molecule of ethanol.

EXAMPLE 13—5-HYDROXY-L-TRYPTOPHYL-5-HYDROXY-L-TRYPTOPHAN (a) Benzyl ester of L-5-hydroxytryptophan 0.2 mol of L-5-hydroxytryptophan is added to 500 ml of benzyl alcohol, and 75 ml of concentrated phosphoric acid are then added slowly, with vigorous stirring. The reaction medium is then heated for 6 hours at 80/90° C. and, after cooling, it is then introduced into iced water containing a small quantity of hydrochloric acid. The excess benzyl alcohol is extracted with ether and the aqueous solution is then neutralized. The product is extracted with ether and, after evaporation, is then purified by chromatography on a silica column in ethyl acetate. This gives 30% of a pure yellow oil.

(b) Benzyl ester of N-benzyloxycarbonyl-5-hydroxy-L-tryptophyl-5-hydroxy-L-tryptophan 40 mmol of the product obtained above according to (a) are added to a solution of 40 mmol of L-N-benzyloxycarbonyl-5-hydroxytryptophan in 500 ml of chloroform, and a solution of 40 mmol of dicyclohexylcarbodiimide in 50 ml of THF is then introduced slowly at +5° C. The mixture is stirred at ambient temperature until the reaction has ended, it is filtered, the filtrate is evaporated and the residue is crystallized from chloroform. This gives the title derivative in the pure state. M.p.=187/8° C.

(c) 5-Hydroxy-L-tryptophyl-5-hydroxy-L-tryptophan hemihydrate

The above product is hydrogenated in isopropyl alcohol at 60° C. under 30 bar in the presence of 5% palladium-on-charcoal. After filtration and evaporation, the residue is recrystallized from water. This gives the title derivative in the form of the hemihydrate of m.p.=360° (dec) and $[\alpha]_D^{25} = -42.2°$ (C=1, ethanol), which, in TLC, shows a single spot of Rf=0.80 in system B and Rf=0.1 in the system toluene 10/ethyl formate 10/formic acid 1/ethanol 1. The NMR spectrum in solution in DMSO-$d_6$ has the following characteristic signals: 11 ppm (m) (2H) phenolic OH; 8.5 ppm (m) (4H) exchangeable; 7.7 to 6.7 ppm (m) (10H) (arom); 4.5 ppm (m) (1H) —CH (NH)—CO; 3.5 ppm (m) (1H) CH (CH$_2$) CO; 3.00 ppm (m) (4H) —CH$_2$—.

EXAMPLE 14—5-HYDROXY-L-TRYPTOPHYL-L-TRYPTOPHAN (a) Benzyl ester of N-benzyloxycarbonyl-5-hydroxy-L-tryptophyl-L-tryptophan A solution of 18.3 g (51.7 mmol) of L-N-benzyloxycarbonyl-5-hydroxytryptophan in 100 ml of pure acetone is added to 15.2 g of the benzyl ester of L-tryptophan, synthesized according to JACS 76, 5781 (1954), in solution in 285 ml of pure chloroform, and then, after the addition of 10.8 g of dicyclohexylcarbodiimide, the mixture is stirred for 48 hours at ambient temperature. After filtration and evaporation of the solvent, the residue is crystallized from chloroform and then recrystallized from isopropyl alcohol.

The pure product shows a single spot in TLC in the system toluene 10/ethyl formate 10/HCOOH 1, of Rf=0.5.

(b) 5-Hydroxy-L-tryptophyl-L-tryptophan 8.5 g of the product described above are subjected to hydrogenolysis in suspension in 200 ml of acetic acid in the presence of 5% palladium-on-charcoal. After filtration and evaporation of the resulting solution, the residue is taken up with benzene and then with ether. This gives 5.0 g of slightly gray crystals showing a single spot in TLC in system A, of Rf=0.50.

EXAMPLE 15—TERT.-BUTYL ESTER OF L-5-HUDROXYTRYPTOPHYL-O-TERT.-BUTYL-L-SERINE (a) Tert.-butyl ester of N-benzyloxycarbonyl-O-tert.-butyl-L-serine 24 g (0.1 mol) of N-benzyloxycarbonyl-L-serine, prepared according to Houben Weyl XV, 1 (49), are suspended in 220 ml of methylene chloride containing 1.5 ml of pure sulfuric acid and 80 g of isobutylene. The apparatus is closed in a leaktight manner and the solution is stirred for 3 days at ordinary temperature. After the excess reactant has been evaporated off, the organic solution is washed with bicarbonate and then dried and evaporated.

(b) Tert.-butyl ester of O-tert.-butyl-L-serine

The above product is subjected to hydrogenolysis in ethanol in the presence of 5% palladium-on-active charcoal. After filtration and evaporation, the title derivative is distilled at t=55° C./0.25 mm with a yield of 55%. The pure product shows only a single spot of Rf 0.1 in the system toluene 10/ethyl formate 1/formic acid 1.

(c) Tert.-butyl ester of N-benzyloxycarbonyl-L-tryptophyl-O-tert.-butyl-L-serine 16.5 g (75 mmol) of the above product are dissolved in 150 ml of pure chloroform and, after the addition of a solution of 76 mmol of dicyclohexylcarbodiimide in 200 ml of chloroform, the mixture is added to a solution of 27 g (75 mmol) of N-benzyloxycarbonyl-L-5-hydroxytryptophan in 150 ml of acetone. The mixture is stirred at ordinary temperature until the condensation has ended. After filtration and evaporation, the residue is taken up with ethyl acetate and the mixture is washed with dilute HCl, with dilute NaOH and then with water. The product is then purified by chromatography on a silica column by elution with a chloroform/acetone mixture. This gives 60% of a pure product showing a single spot of Rf=0.9 by TLC in system A.

(d) Tert.-butyl ester of L-5-hydroxytryptophyl-O-tert.-butyl-L-serine 6.36 g of the above product are hydrogenated in 65 ml of acetic acid. After filtration and evaporation, the residue is taken up with benzene and then with ether. This gives 90% of the title derivative in the pure state, which shows a single spot in TLC in system A, of Rf=0.60.

The NMR spectrum recorded in DMSO-$d_6$ has the following characteristic signals: 1.1 and 1.4 ppm 2 (s) (9H); 3 to 3.6 ppm (m) (5H); 2—CH$_2$— and CH(NH$_2$)—COOH; 4.5 ppm (m) (1H)CH(NH—)CH$_2$; 5.8 ppm (m) NH$_2$; 6.6 to 7.4 ppm (5H) (arom); 8.3 ppm (m) 1H —NH—. $[\alpha]_D^{25} = -10°$ (C=1, DMF).

EXAMPLE 16—L-5-HYDROXYTRYPTOPHYL-L-SERINE 3.5 g of the above product are added to 20 ml of a saturated solution of hydrochloric acid in acetic acid. After one hour at ordinary temperature, the mixture is introduced into 150 ml of ether and the precipitate is filtered off. This gives the title derivative in the form of a white to pale gray crystalline product showing a single spot in TLC in system A, of Rf=0.20. The NMR spectrum recorded in DMSO-$d_6$ has the following characteristic signals: 7.2 and 6.5 ppm (m) (4H) arom; 4.5 ppm (m) (2H) —$\underline{CH}$(NH)—CO; 3.7 ppm (m) (2H), $\underline{CH}$—CH$_2$—O; 3.1 ppm (m) (2H) CH$_2$OH.

EXAMPLE 17—L-5-HYDROXYTRYPTOPHYL-L-SERINE VIA THE CYANOMETHYL ESTER OF THE DANE SALT OF L-5-HYDROXYTRYPTOPHAN (a) Cyanomethyl ester of L-N-(1-methyl-2-acetylvinyl)-5-hydroxytryptophan 17.6 g (80 mmol) of L-5-hydroxytryptophan are dissolved in 80 ml of dimethylformamide, 80 mmol of tetramethylguanidine are added and the mixture is stirred for 30 minutes at ordinary temperature.

8.0 g (80 mmol) of acetylacetone are then introduced into the reaction solution, followed, after stirring for 2 hours at ordinary temperature, by 6.1 g (80 mmol) of chloroacetonitrile. The mixture is stirred at ordinary temperature until the reaction has ended, i.e. for about 48 hours. The reaction medium is then introduced into an aqueous solution of sodium bicarbonate and the mixture is extracted with ethyl acetate. After the organic solution has been washed with a dilute solution of sodium bicarbonate and then with water, it is dried over sodium sulfate and evaporated to dryness. This gives 22.9 g (84%) of the title derivative, which, in TLC, shows a single spot of Rf=0.9 in system A and Rf=0.4 in the system chloroform 5/ethyl acetate 20. The NMR spectrum recorded in CD$_3$CN has the following characteristic signals: 6.6 to 7.3 ppm (m) (5H) (arom); 5.0 ppm (s) (1H)=CH—CO; 4.8 ppm (s) (2H) OCH$_2$CN; 4.6 ppm (m) (1H) CH$_2$$\underline{CH}$(NH) COO; 3.2 ppm (m) (2H) $\underline{CH_2}$—CH(NH)COO; 2 ppm (2s) (6H) $\underline{CH_3}$—C=, $\underline{CH_3}$C=O.

(b) O-Tert.-butyl ester of N-(1-methyl-2-acetylvinyl)-5-hydroxy-L-tryptophyl-O-tert.-butyl-L-serine 13.68 g (63 mmol) of the O-tert.-butyl ester of O-tert.-butyl-L-serine, prepared according to Example 15(b), and 21.48 g (63 mmol) of the reactive ester of L-5-hydroxytryptophan, prepared above according to (a), are added to a mixture of 60 ml of acetonitrile and 100 ml of ethyl acetate to which 0.1 ml of glacial acetic acid has been added. The mixture is then stirred at ordinary temperature until the condensation has ended. After a small quantity of insoluble material has been filtered off, the filtrate is evaporated to dryness and the residue is purified by chromatography on a silica column, elution being carried out with a chloroform/ethanol mixture.

The title derivative is thus isolated in the pure state with a yield of nearly 40%. Chromatography on a thin layer of silica in the system toluene 10/ethyl formate 10/formic acid 1 shows a single spot of Rf=0.40.

(c) 5-Hydroxy-L-tryptophyl-L-serine 3.4 g (6.8 mmol) of the derivative obtained above according to (b) are dissolved in 25 ml of acetic acid saturated with hydrochloric acid, the solution is stirred for a few hours at ordinary temperature, the product is then precipitated in excess ethyl ether and filtered off and the precipitate is dried to give the title derivative in the pure state, which is identical to the product obtained according to Example 16.

EXAMPLE 18—5-HYDROXY-L-TRYPTOPHYL-L-ARGININE (a) Benzyl ester of N-benzyloxycarbonyl-5-hydroxy-L-tryptophyl-ω-nitro-L-arginine A solution of 22.7 g (70 mmol) of the benzyl ester of ω-nitro-L-arginine in 170 ml of chloroform is added to a solution of 24.15 g (68.2 mmol) of N-benzyloxycarbonyl-L-5-hydroxytryptophan in 135 ml of acetone.

A solution of 70 mmol of dicyclohexylcarbodiimide in chloroform is then introduced and the mixture is stirred at ordinary temperature until the reaction has ended. After the dicyclohexylurea has been filtered off and the solvent evaporated off, the residue is taken up with ethyl acetate and the mixture is then washed with normal hydrochloric acid, with sodium hydroxide solution and then with water. After drying, evaporation and taking up with ether, the title derivative is obtained in the pure state, showing, in TLC, a single spot of Rf=0.6 in acetonitrile. NMR spectrometry in CD$_3$CN shows the following characteristic signals: 7.2 ppm (s) (10H) benzyl; 7.4 to 6.6 ppm (m) (5H) (arom); 5.0 ppm (2×s) (4H) 2×—CH$_2$ benzyl; 4.5 ppm (m) (2H) 2—$\underline{CH}$(NH) CO; 3.2 ppm (m) (4H).

(b) 5-Hydroxy-L-tryptophyl-L-arginine 3.7 g (5.7 mmol) of the derivative obtained according to (a) are subjected to hydrogenolysis in solution in acetic acid in the presence of 5% palladium-on-charcoal. After filtration and evaporation of the solvent, the product is taken up in a water/ethanol mixture to give the title derivative in the pure state. TLC of this derivative shows a single spot of Rf=0.05 in the system toluene 10/ethyl formate 10/formic acid 1. The NMR spectrum recorded in DMSO-$d_6$ shows the following characteristic signals: 7.5 to 6.5 ppm (m) (4H) (arom); 4.4 ppm (m) (2H) —CH—(NH)CO; 3.2 ppm (m) (4H) CH$_2$—CH(NH)CO and N—$\underline{CH_2}$—; 1.7 ppm (m) (4H) —$\underline{CH_2}$—$\underline{CH_2}$—.

EXAMPLE 19—5-HYDROXY-L-TRYPTOPHYLGLYCINE 0.1 mol (33.7 g) of benzyl glycinate paratoluenesulfonate (prepared according to ZERVAS, Journal of Organic Chemistry 22, 1520 (1957)) is dissolved in 500 ml of pure chloroform containing 0.1 mol of triethylamine. After 30 minutes, a solution of 34 g (0.1 mol) of L-N-benzyloxycarbonyl-5-hydroxytryptophan in 200 ml of acetone is added and a solution of 0.1 mol of dicyclohexylcarbodiimide in 50 ml of chloroform is then added at +5° C. The mixture is stirred at ordinary temperature until the reaction has ended (about 24 hours). It is then filtered, the filtrate is evaporated, the residue is taken up with methyl ethyl ketone and the mixture is washed with acidified water, with dilute sodium hydroxide solution and finally with water. After drying and evaporation, the residue is crystallized from a chloroform/ethanol mixture. This gives a TLC-pure product of m.p.=114° C. and $[\alpha]_D^{25}$=−31.2° (C=1, acetone), which is hydrogenated in solution in acetic acid in the presence of palladium. When the hydrogenation has ended, the mixture is filtered, the filtrate is evaporated and the residue is again made into a paste in acetone several times and then crystallized from ethanol. This gives the title derivative in the form of a solvate containing one molecule of ethanol, of m.p. 178°, which, in TLC, shows a single spot of Rf=0.15 in system B. $[\alpha]_D^{25} = 27.7°$ (C=1, DMF), NMR spectrum recorded in D$_2$O: 7.5 to 6.8 ppm (m) (4H) (arom); 4.8 ppm broad band, mobile H; 4.2 ppm (m) (1H) —C$\underline{H}$ CONH; 3.7 ppm (q) (2H), CH$_3$C$\underline{H}_2$OH; 3.7 ppm (d) (2H) —CH$_2$—CH—; 3.2 ppm (d) (2H) NHC$\underline{H}_2$CO—; 1.1 ppm (t) (3H) C$\underline{H}_3$—CH$_2$—OH;

EXAMPLE 20—5-HYDROXY L-TRYPTOPHYL-γ-AMINOBUTYRIC ACID (a) Tert.-butyl N-benzyloxycarbonyl-5-hydroxy-L-tryptophyl-γ-aminobutyrate 85 mmol of N-benzyloxycarbonyl-5-hydroxy-L-tryptophan and 85 mmol of tert.-butyl γ-aminobutyrate are dissolved in 170 ml of acetone and 300 ml of pure chloroform. A solution of 17.7 g (86 mmol) of dicyclohexylcarbodiimide in 80 ml of chloroform is then added and the mixture is stirred at ordinary temperature until the condensation has ended. After evaporation, taking up with ethyl acetate and the customary treatment, 40 g of a crude product are obtained, which are purified by chromatography on a silica column, elution being carried out with a methylene chloride/acetone mixture. This gives 48% of a pure product showing a single spot in TLC on Kieselgel in the system chloroform 20/acetone 6, of Rf=0.45. The NMR spectrum is recorded in solution in CDCl$_3$: 8.4 ppm (s) (1H) —OH; 7.3 ppm (s) (5H) benzyl; 7.2 to 6.6 ppm (m) (4H) arom; 6.4 ppm (m) (1H) and 5.9 ppm (d) (1H) —NH; 5 ppm (s) (2H) CH$_2$—Ph; 4.4 ppm (m) (1H) CH(NH)—CO; 3.1 ppm (m) (4H) C$\underline{H}_2$—CH(—NH)CO and NH C$\underline{H}_2$; 2.1 to 1.8 ppm (m) $\overline{4H}$: CH$_2$—CH$_2$; 1.4 ppm (s) (9$\overline{H}$) tert.-butyl.

(b) Tert.-butyl 5-hydroxy-L-tryptophyl-γ-aminobutyrate

The product obtained above is hydrogenated in 120 ml of acetic acid in the presence of 1.2 g of 5% palladium/C. After the catalyst has been filtered off, the filtrate is evaporated to dryness and the residue is taken up with ether. This gives the title derivative in the pure state with a quantitative yield.

Its TLC on Kieselgel in system A shows only a single spot of Rf=0.5. Its NMR spectrum recorded in DMSO-d$_6$ has the following characteristic signals: 10.5 ppm (s) (1H) NH indole; 8 ppm (1H) (m)—OH; 7.2 to 6.5 ppm (m) (4H) arom; 3.5 ppm (1H) (m) C$\underline{H}$(NH—)CO; 3 ppm (m) (2H) C$\underline{H}_2$—CH(NH)—; 2.9 ppm (m) (2H) NH—C$\underline{H}_2$; 2.2 to 1.3 ppm (m) 6H; 1.4 ppm (s) (9H)- —O—t—butyl.

(c) 5-Hydroxy-L-tryptophyl-γ-aminobutyric acid

The product obtained above is dissolved in 8 ml of acetic acid saturated with hydrochloric acid, at about 10° C., and the solution is stirred for two hours at ordinary temperature and then evaporated to dryness. The pure product is purified by chromatography on Sephadex G 10 gel in N/10 formic acid. This gives the title derivative in the pure state. Its chromatography on a Kieselgel plate shows only a single spot of Rf=0.3 in system A. NMR spectrum in DMSO-d$_6$: 8.4 ppm (s) (2H) —NH; 7.2 to 6.5 ppm (m) (4H) arom; 3.8 ppm (m) (1H) C$\underline{H}$(NH)—CO; 3.1 ppm (m) (4H) C$\underline{H}_2$CH(NH) and NHC$\underline{H}_2$; 2.2 ppm (dd) (2H) —CH$_2$—; 1.7 ppm (m) (2H) —C$\underline{H}_2$—.

EXAMPLE 21—5-HYDROXY-L-TRYPTOPHANAMIDE HYDRATE 0.115 mol (69.3 g) of the pentachlorophenyl ester of L-N-benzyloxycarbonyl-5-hydroxytryptophan is dissolved in 300 ml of anhydrous ethanol containing 20% of ammonia. After one night at +5° C., the phenol is filtered off and washed with ether and the solution is evaporated.

The residue is made into a paste again in isopropyl ether and the pure Z-Trp(5 OH)NH$_2$ of m.p.=171° C. is filtered off with an almost quantitative yield. This product is hydrogenated in isopropyl alcohol in the presence of palladium-on-charcoal. After filtration and evaporation, the product is taken up in water, chromatographed on gel and then lyophilized. TLC in A shows a single spot at Rf=0.45. The NMR spectrum recorded in DMSO-d$_6$ has the following signals: 10.5 ppm (s) broad (1H), OH phenol; 7.4 to 6.4 ppm (m) (7H), 5 arom and 2 mobile H; 4.3 ppm broad band, H$_2$O and NH$_2$; 3.4 ppm (m) (1H) C$\underline{H}$—CO; 2.8 ppm (m) (2H) —CH$_2$—; the infra-red spectrum (KBr) contains a strong absorption from 3500 to 2500 (strong hydrogen bonds) and a characteristic band at 1670 cm$^{-1}$. $[\alpha]_D^{25} = -8.47°$ (C=1, ethanol).

EXAMPLE 22—METHYL ESTER OF 5-HYDROXY-L-TRYPTOPHYL-L-HISTIDINE

A solution of 50 mmol of N-benzyloxycarbonyl-5-hydroxy-L-tryptophan in 150 ml of acetone is added to 50 mmol of the methyl ester of L-histidine, prepared according to N. C. DAVIS (J. Biol. Chem. 223, 935 (1956)), in solution in 200 ml of acetonitrile. The mixture is treated at 0° C. with a solution of 52 mmol of DCC in 100 ml of chloroform. The mixture is kept at ambient temperature until the reaction has ended. After evaporation, taking up with ethyl acetate and the customary treatment, 80% of a crude product is obtained, which is purified by chromatography on silica, elution being carried out with a methylene chloride/acetone mixture.

The purified product is subjected to hydrogenolysis in solution in methanol in the presence of palladium/-charcoal. After filtration and evaporation of the solvent, the product is purified by chromatography on G 10 gel, elution being carried out with M formic acid. This gives the title derivative as the formate. TLC of the product shows a single spot of Rf 0.3 in system A. In MNR, the following characteristic signals are observed (DMSO-d$_6$): 9.7 ppm (m) (1H) NH indole; 8.7 ppm (s) (1H) NH imidazole; 7.5 and 6.5 ppm (m) (4H) indole; 7.5 (s) (1H) imidazole; 4.5 ppm (m) (1H) CH—(NH)—CO; 4.2 ppm (m) (1H) CH(NH$_2$)—CO; 4.0 ppm (s) (3H) OCH$_3$; 3.5 ppm (m) (4H) —CH$_2$—.

These new products according to the present invention exhibit anxiolytic, analgesic, antihypertensive and antiepileptic activities and thus prove to be remarkable drugs for use in human or veterinary therapy.

The pharmacological review which follows shows the activity of these compounds on the central nervous system.

Biochemical analysis of the brain levles of L-5-hydroxytryptophan (L-5-HTP), serotonin (5-HT) and its first metabolite, 5-hydroxyindoleacetic acid (5-HIAA), was carried out one hour after the administration of a single dose to adult rats by the technique of CURZON and GREEN. Three doses were studied, i.e.

10, 25 and 50 mg/kg, 10 animals being used per dose. Table I below indicates the percentage increases in 5-HTP, 5-HT and 5-HIAA relative to the levels found in the control animals:

TABLE I

| EXAMPLE | L-5-HTP at doses of | | | 5-HT at doses of | | | 5-HIAA at doses of | | |
|---|---|---|---|---|---|---|---|---|---|
| | 10 mg/kg | 25 mg/kg | 50 mg/kg | 10 mg/kg | 25 mg/kg | 50 mg/kg | 10 mg/kg | 25 mg/kg | 50 mg/kg |
| 2 | 200 | 600 | 1000 | 5 | 5 | 10 | | | |
| 3 | 100 | 400 | 1100 | 10 | | 200 | 50 | 150 | 200 |
| 4 | 200 | 550 | 2500 | 5 | 10 | 60 | | | |
| 5 | 200 | 450 | 1200 | 12 | 10 | 40 | 55 | 160 | 170 |
| 6 | | | | | 5 | 5 | | | |
| 7 | 10 | | 30 | | | | 10 | 20 | 20 |
| 8 | 200 | 3000 | 2400 | | 5 | | 75 | 140 | 400 |
| 9 | 300 | 900 | 1700 | 12 | 40 | 45 | 70 | 250 | 320 |
| 10 | 200 | 600 | 2000 | | 12 | 45 | 55 | 100 | 350 |
| 11 | 200 | 700 | 1600 | 10 | | 20 | | 150 | 300 |
| 12 | 170 | 500 | 1100 | | | 25 | | 140 | 180 |
| 13 | | 50 | 50 | 5 | 5 | | | | 10 |
| 14 | 50 | 100 | 200 | | 12 | 10 | | | |
| 15 | 200 | 400 | 900 | | | | | 60 | 150 |
| 16 | 170 | | 900 | | | 15 | 10 | 30 | 150 |
| 18 | 100 | 300 | 500 | 12 | 30 | 30 | 10 | 15 | 15 |
| 19 | | 700 | 1300 | 30 | 12 | 30 | 75 | 170 | 350 |
| 20 | 60 | 200 | 400 | 5 | 5 | 15 | 40 | 100 | 150 |
| 21 | 125 | 250 | 700 | | | 20 | 30 | 50 | 170 |
| 22 | | 200 | 300 | | 15 | 15 | 40 | 140 | 300 |

In vivo, all the compounds according to the invention proved to be analgesics at doses of between $1.5 \cdot 10^{-3}$ and $1 \cdot 10^{-6}$ mol/kg in the heating plate test according to A. LESPAGNOL and J. MERCIER (Ann. Phar. Fr. (1950) 8, 241-251), the analgesic effect lasting for more than two hours after administration.

Furthermore, the derivatives according to the invention have a very much lower acute toxicity to mice than L-5-HTP. Thus, the $LD_{50}$ values of these compounds administered orally to mice are greater than 1500 mg/kg for the most toxic and can even be as much as 3000 mg/kg.

It is apparent from the present description that the derivatives according to the invention offer particularly advantageous pharmacological and clinical activities against all complaints in which the serotoninergic system is deficient, and they consequently represent drugs which make it possible to cure the diseases resulting from this disorder, in view of their high activity and their low toxicity.

As is also apparent from the above, the invention is in no way limited to those methods of carrying its out, those embodiments and those methods of application which have now been described in greater detail; on the contrary, it encompasses all the variants which may occur to those skilled in the art, without exceeding the field or scope of the present invention.

What is claimed is:

1. Dipeptides of L-5-hydroxytryptophan of the general formula I below:

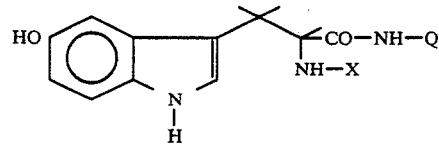

wherein X is hydrogen or a lower acyl radical and Q is a free or esterified aminoacid radical selected from the group consisting of alanine, valine, leucine, isoleucine, proline, phenylalanine, tryptophan, methionine, glycine, serine, threonine, cysteine, tyrosine, asparagine, glutamine, aspartic acid, glutamic acid, lysine, and histidine, and their pharmaceutically compatible addition salts with acids or base.

2. The dipeptides of claim 1, wherein Q is a dicarboxylic aminoacid radical selected from the group consisting of aspartic acid and glutamic acid.

3. The dipeptides of claim 1, wherein Q is a basic aminoacid radical selected from the group consisting of lysine and histidine.

4. The dipeptides of claim 1, wherein Q is an —OH containing aminoacid radical selected from the group consisting of serine, threonine and tyrosine.

5. The dipeptides of claim 1, 2, 3 or 4, wherein the reactive groups of said free or esterified aminoacid radical are substituted.

6. A composition for combating disorders of the serotoninergic system comprising a therapeutically effective amount of at least one of the dipeptides of claim 1.

* * * * *